(12) United States Patent  
Buckman et al.

(10) Patent No.: US 7,507,216 B2
(45) Date of Patent: Mar. 24, 2009

(54) SPLINT SYSTEM AND METHOD OF USE

(75) Inventors: Robert F. Buckman, Radnor, PA (US);
Jay A. Lenker, Laguna Beach, CA (US);
Donald J. Kolehmainen, Laguna Niguel, CA (US)

(73) Assignee: Damage Control Surgical Technologies, Inc., Laguna Beach, CA (US)

( * ) Notice: Subject to any disclaimer, the term of this patent is extended or adjusted under 35 U.S.C. 154(b) by 214 days.

(21) Appl. No.: 11/397,499

(22) Filed: Apr. 4, 2006

(65) Prior Publication Data

US 2006/0184083 A1 Aug. 17, 2006

Related U.S. Application Data

(63) Continuation-in-part of application No. 10/764,123, filed on Jan. 24, 2004, now Pat. No. 7,022,094.

(51) Int. Cl.
*A61F 5/00* (2006.01)

(52) U.S. Cl. .............................. 602/32; 602/13; 602/23

(58) Field of Classification Search .................. 602/32, 602/5, 13, 38, 40, 12, 19–36; 128/84, 85, 128/86, 846, 869, 882, 856, 870, 878; 606/241, 606/237, 54, 56, 900; 2/44, 311; 119/863; 441/55–67, 107, 91
See application file for complete search history.

(56) References Cited

U.S. PATENT DOCUMENTS

| | | | | |
|---|---|---|---|---|
| 2,319,400 | A | 5/1943 | Hartmann et al. | |
| 2,604,889 | A * | 7/1952 | Erickson | 602/35 |
| 3,906,942 | A * | 9/1975 | Lumb et al. | 602/40 |
| 4,608,971 | A | 9/1986 | Borschneck | |
| 4,649,907 | A | 3/1987 | Whitehead et al. | |
| 4,867,140 | A * | 9/1989 | Hovis et al. | 601/152 |
| 5,162,039 | A | 11/1992 | Dahners | |
| 5,403,266 | A * | 4/1995 | Bragg et al. | 602/5 |
| 5,897,555 | A | 4/1999 | Clyburn et al. | |
| 5,916,185 | A * | 6/1999 | Chitwood | 602/18 |
| 6,045,525 | A * | 4/2000 | Chitwood | 602/36 |
| 6,716,711 | B1 * | 4/2004 | Racanelli | 438/321 |
| 6,719,711 | B1 * | 4/2004 | Islava | 602/13 |
| 6,786,882 | B2 * | 9/2004 | Slishman | 602/36 |
| 2004/0049139 | A1 * | 3/2004 | Craciunescu | 602/13 |
| 2004/0171973 | A1 * | 9/2004 | Branch | 602/13 |

* cited by examiner

*Primary Examiner*—Patricia M Bianco
*Assistant Examiner*—James M Robinson

(57) ABSTRACT

Devices and methods are disclosed for achieving control and stabilization of bone fractures in mammals, most specifically humans. Stabilization and traction is often required to support fractured bones of the arms or legs. The devices and methods disclosed herein are especially useful in the emergency or military setting. The devices utilize a collapsible frame or inflatable member that may be expanded and locked into position. The frame or inflatable member is fabricated primarily from polymeric materials with low radiodensity. The limb contact regions are adjustable to fit a wide variety of limb sizes and fracture locations. The traction applied by the splint is adjustable, controllable and measurable. The traction splint is sufficiently compact that it will fit in a compartment of most ambulances and emergency rescue vehicles, thus making it more available for use than standard traction splints in use today. The traction splint is either a separate device or integrated into a backboard.

20 Claims, 8 Drawing Sheets

SPLINT SYSTEM AND METHOD OF USE

PRIORITY CLAIM

This application is a continuation-in-part of U.S. patent application Ser. No. 10/764,123, filed Jan. 24, 2004, now U.S. Pat. No. 7,022,094, the entirety of which is hereby incorporated herein by reference.

FIELD OF THE INVENTION

This invention relates to methods and devices for treating fractures of bones in the arms and legs and is particularly well suited for immobilizing and providing traction for fractured bones in an emergency or trauma situation.

BACKGROUND OF THE INVENTION

Fractures of the bones in the arms and legs are a frequent occurrence throughout the United States and internationally. When a fracture occurs, it generally takes place outside the hospital setting so treatment is administered by emergency caregivers such as emergency medical technicians (EMT) and paramedics. Emergency medical technicians and paramedics travel in ambulances, mobile intensive care units (MICU), which are highly equipped ambulances, and helicopters. These vehicles have limited space. The equipment they carry must be compact in order to fit in the cabins of these vehicles.

When a fracture of a bone occurs, the bones either separate and become misaligned or they remain in place but with a split or fracture at the site of injury. In extreme cases called compound fractures, bones separate and become misaligned, the bone projects out through the skin of the patient. A complete fracture of a femur causes the two separate bone ends to pull against each other so that the ends pass each other. The muscle contracts in spasm and a large amount of blood pools in the leg. Potential damage to nerves, muscle, and major blood vessels in the leg needs to be avoided by stabilization of the fracture and relief of axial compressive forces on the bone.

Treatment of these fractures generally involves initial diagnosis of the injury, stabilization of the broken bone, and application of traction force. Application of traction force is especially useful to treat a compound fracture or when the bones become misaligned and cause the intense pain, shock, and potential for damage to adjacent structures such as vasculature and nerves.

Devices currently exist for applying traction to broken bones of the arms or legs. Exemplary devices include Sager Splints and Hare Traction Splints. These devices are large, heavy, cumbersome, and do not fit on helicopters and take up excessive space on ground emergency vehicles such as ambulances and mobile intensive care units (MICU). Of significant importance is the fact that these current traction splints are fabricated from metallic components and are radiopaque. The radiopaque mass of the splint hinders radiographic or X-Ray analysis of the fracture.

The current method of lower extremity bone fracture stabilization and therapy comprises placing the patient on a stretcher, litter or backboard. Diagnosis of a femur fracture triggers the application of a current traction splint as a separate procedure from placing the patient on the backboard. The placement of a traction splint involves the steps of rolling the patient away from the affected side. Next, the splint is placed so that the ischial contact bar is engaged with the ischium of the pelvis. The injured lower extremity is laid upon the cross-straps of the current traction splint. The traction splint is extended to its desired length. The foot strap is wrapped around the lower leg and is engaged against the top of the foot. The rings on the bottom of the foot strap are affixed to a hook attached to a ratcheting roller device to apply tension to the foot. Elastic straps are wrapped around the side of the leg to hold the leg in place relative to the traction splint. This process is extremely time consuming, complicated, and cumbersome, and the patient suffers much discomfort until the traction is finally applied.

New devices and methods are needed to permit rapid fluoroscopic or X-Ray analysis of broken bones in the arms and legs while a traction splint is in place. In addition, improved devices are necessary in order to permit traction devices and splints to fit in the restricted space available on emergency vehicles. The traction splint would be even more convenient and space-efficient if it were incorporated into a backboard or gurney.

SUMMARY OF THE INVENTION

This invention relates to improved devices and methods for initial treatment of fractures of the bones in the arms and legs. The present invention is a traction splint that is fabricated primarily from non-metallic, minimally radiodense components. The use of non-metallic components allows the splint to be minimally radiopaque. Under X-Ray evaluation, the splint will show as a shadow but will not obscure the details of the bone in such a way as to hinder reading and analysis of the X-Ray image. The traction splint can comprise inflatable components that are highly foldable and compact and yet can be inflated to provide both support and traction on a fractured arm or leg.

A primary aspect of the invention is collapsibility of the splint structure so as to be highly compact in its storage state. The splint may controllably be opened from its collapsed or compact state to its deployed or expanded state to support a broken arm or leg. The splint, once opened, may be locked in place to maintain a stable configuration. The splint, according to another aspect of the invention, further comprises an adjustable and lockable hinge area at or near its central region to permit articulation as needed to treat the patient. In a further embodiment of the invention, the splint is adjustable to fit a wide range of arm or leg sizes and fracture locations. In yet another embodiment, a controllable traction force is generated by the splint. The splint comprises a readout, gauge or meter that permits monitoring of the traction force applied by the splint. The traction force is generated by a mechanism that is configured not to project beyond the bottom of the splint, thus minimizing overall length of the splint in the collapsed and expanded or deployed configuration. In this embodiment, the traction splint applies tension force to the limb by acting in compression, rather than in tension, as does a pulley system.

In yet another embodiment of the invention, the traction splint comprises an integral backboard or stretcher. The backboard traction splint combination relies on the backboard to provide the longitudinal support structure for offset components that affix around the appendage to generate the traction and injury stabilization of that appendage. The offset components ride in slots within the backboard. The offset components can be locked down at discreet or continuously variable locations on the backboard.

It is preferable, in lieu of an upper traction member, to provide a high friction region between the back of the patient and the backboard for the upper traction element. In another embodiment, the upper traction element comprises a standoff that further comprises padding and interfaces with the ischium of the pelvis. Straps, or a cuirass, that further comprise belts and buckles, clips, VELCRO® or other hook and loop fabric fastener, or other locking devices, ensure continued engagement of the upper and lower traction elements. The padding is comprised of foam, fabricated from materials such as, but not limited to, silicone elastomer, polyurethane, polyester, polyvinyl chloride, and the like. The upper traction element, in another embodiment, comprises padded posts or projections that extend outward to contact the armpits of the patient. The upper traction elements, if utilized, are disposed within a longitudinal or lateral track within the splint. The high friction can further be generated, or enhanced, by inflating a proximal support member, which is wrapped and fastened to a limb region, to generate inward gripping and support force to the limb region.

The lower traction element is, preferably, a C-shaped cuirass that is padded and openable to allow it to fit around the leg. The cuirass is then closed and locked to provide a locking element with the leg. Padding on the lower traction element provides stress equalization against the leg and minimizes high stress points that might be painful or cause minor tissue damage to the patient. Ideally, the lower traction element encircles the ankle and exerts force against the top of the foot. The lower traction element and upper traction element are fixtured to project upward from the backboard at the correct lateral location on the backboard. These traction elements are inserted through holes or detents in a longitudinal slot in the backboard and locked in place with devices such as, but not limited to, offset cams, set-screws, bayonet mounts and the like. The backboard component of the splint is fabricated from non-metallic components such as, but not limited to, carbon fiber, polypropylene, polyethylene, polyurethane, polycarbonate, and the like. The polymeric materials are preferably further strengthened with the use of glass fibers, Kevlar, polyamide and the like. Friction between the traction splint and limb can be generated, or enhanced, by inflating a distal support member, which is wrapped and fastened to a limb region, to generate inward gripping and support force to the limb region.

The upper and lower traction elements, in a further embodiment, ca\n be integral to the backboard and fold into the backboard when not in use. The traction elements are unfolded out of the backboard when needed. In another embodiment, the traction splint can be deflated and fold flat against a backboard for anticipated use. Small pockets or storage areas can be comprised by a typically thin backboard, wherein these pockets or storage areas can hold a collapsed, inflatable traction splint.

In an embodiment of the invention, the traction force is generated by apparatus such as, but not limited to, spring-loaded members, a jack-screw, a pulley apparatus or hydraulic, pneumatic, or fluidic force. The pulley apparatus preferably is disposed on the bottom side of the backboard and is routed around the bottom or lower end of the backboard to provide tension on the lower traction element engaged with the foot. In the most preferred embodiment, the traction apparatus is not a pulley arrangement or structure in tension, but is a bar, bellows, airbag, liquid or gel filled bag, or other structural element in compression that pushes the leg or arm away from the torso.

In all the elements for generating traction, the amount of tension is pre-determined. The preferred amount of traction force should range between 1 and 50 pounds, and preferably the range should be between 5 and 25 pounds, and most preferably, the range should be 10 to 20 pounds. The traction splint optionally comprises a gauge to measure the amount of traction force being generated.

In yet another embodiment, the backboard with the integral traction splint further comprises a section that selectively folds out, or inflates outward, to elevate one or both legs or arms, collectively limbs. The limb elevation region comprises optional padding. The limb elevation region further comprises an optional articulation region that permits the knee to bend. The amount of limb elevation and limb articulation may be variable and controllable or they may be pre-set to certain preferred levels. A similar feature optionally is provided for arm elevation and articulation if required.

In yet a further embodiment of the traction splint with the integral backboard, the traction elements are releasably disposed within slots in the backboard. The traction elements are removable from the backboard so as to stay with the patient. The removable traction splint traction elements further comprise a removable longitudinal support that is normally integral to the backboard or a separately added piece. The separately added longitudinal support is attached to the traction elements once the correct amount of traction and appendage orientation have been determined. The longitudinal support is added through lockable elements in the traction elements to maintain their orientation and traction following removal from the backboard. Alternatively, the longitudinal support is that region of the backboard that holds the traction elements. This region is capable of being unlocked, detached, or removed from the backboard so as to stay with the traction elements.

In a further embodiment, the traction splint is provided integral to the backboard. The traction elements slide up and down along the backboard in a groove or slot. The traction elements have the capability of locking into the groove or slot in the backboard. When the patient is to be removed from the backboard, the upper traction element, a longitudinal element, and the lower traction element are separated from the backboard and stay with the patient. The upper and lower traction elements and the longitudinal support are disposable. A new disposable upper traction element, lower traction element and longitudinal support are reloaded onto the backboard or stretcher for the next case. This disposability allows for the traction splint to stay with the patient throughout their early therapy and for the stretcher or backboard to be immediately reused on another patient with a new disposable traction apparatus.

In yet another embodiment of the invention, an adult and a pediatric backboard traction splint combination is provided due to the extreme differences in sizes of these types of patients. In another embodiment, the backboard telescopes to adjust to the size of the patient and to provide compactness during storage. The telescoping backboard is provided with fasteners to allow for locking of the backboard at predetermined length intervals, or in another embodiment, at any continuously variable or adjustable length.

Using the methods of the present invention, a patient is placed directly upon the backboard. The lower, or distal, traction element is folded out and placed in contact with the top of the foot and locked in place so as to be able to provide axial caudal traction force on the foot. The lower traction element is advanced axially caudally until the desired traction force is applied to the foot. The leg is optionally elevated prior to applying the traction.

This apparatus is suitable for various lower extremity fractures including fractures of the tibia and fibula as well as fractures of the femur. The apparatus is also suitable for stabilization and traction of ligamentous injuries of the knee. The inflatable version of the traction splint is suitable for both upper extremity fractures, such as in an arm, and lower extremity fractures, such as in a leg.

The immobilization of hip fractures, one of the most common fractures in the world, is a problem since the ischial bar of current traction splints put pressure on the region of the hip that might have been damaged due to a hip fracture. The current invention is preferable to current devices in that it need not put pressure on the ischium because the upper traction element is comprised of simple friction between the back of the patient and the stretcher or by pads under the armpits. In this embodiment, the inflatable embodiment can provide for both support and traction to the region of the hip by gripping the torso of the patient at its proximal end and the leg of the patient at its distal end. The flexible, conformable nature of the inflatable traction splint is beneficial in supporting and providing traction on the injured hip region.

In a further embodiment, where the patient with a hip fracture or lower extremity fracture is removed from the stretcher or backboard, a pad or padded element that retains frictional contact with the torso, in a region such as the buttox and back, remains with the patient after removal from the backboard. The pad, friction pad, or padded element provides optimal upper traction force on the patient without the need for an ischial bar. A strap or other element provides force to coerce the patient against the friction pad.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

DETAILED DESCRIPTION OF THE INVENTION

In accordance with one or more embodiments of the present invention, a traction splint, packaging and accessory components are described herein. In order to fully specify this preferred design, various embodiment specific details are set forth, such as the number and makeup of the limb-contacting elements and methods of generating traction. It should be understood, however that these details are provided only to illustrate the presented embodiments, and are not intended to limit the scope of the present invention. By way of definition, the words axial and longitudinal refer to the long axis of a limb being placed in traction. The lateral direction is generally orthogonal to the long axis of the limb being placed in traction.

Figure 1A:
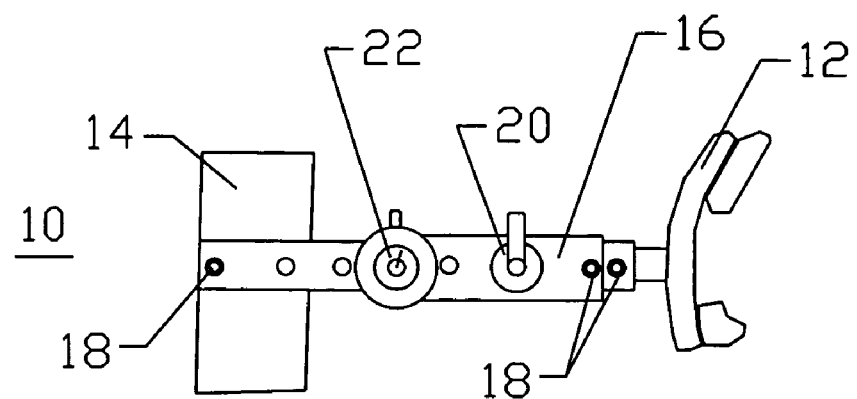
FIG. 1A illustrates a side view of a leg traction splint in its collapsed or storage configuration, according to an embodiment of the invention.

FIG. 1A illustrates a traction splint 10 of the present invention in its collapsed configuration. The traction splint 10 further comprises a distal support member 12, a proximal support member 14, an axial support 16, one or more axial support locks 18, a traction force generating mechanism 20 and a traction force measuring mechanism 22.

Further referring to FIG. 1A, the distal support member 12 is affixed to the axial support 16 at or near its distal end. The proximal support member 14 is affixed to the proximal end of the axial support 16. The axial support locks 18 are affixed to at least one component of the axial support 16 and selectively engage with other components of the axial support 16. The force generating mechanism 20 is affixed to the axial support 16 and generates a controlled axial expansion of the axial support 16 or axial movement of either the proximal support member 14 or the distal support member 12 relative to the axial support 16. The force measuring mechanism 22 is affixed to the axial support 16 or between the axial support 16 and either the distal support 12 or the proximal support 14. The force measuring mechanism 22 may be permanently affixed to the structure or it may be removably affixed to the traction splint 10 so that it can be removed once the amount of traction force has been determined.

Referring to FIG. 1A, the axial support locks 18 in this embodiment are spring-loaded pins, preferably with a hemispherical end, affixed to the inner telescoping member or members of the axial support 16. They project outward through holes the outer telescoping member or members of the axial support 16. To telescope the axial support 16, one depresses the spring-loaded pin to a position inside that of the outer telescoping member of the axial support 16. The axial support inner and outer members are then moved axially to the desired location. The spring-loaded pin advances under its own force outward through another hole in the outer support member. FIG. 1A depicts three such spring-loaded pins and a plurality of holes in the axial support 16 through which the pins can be aligned. This configuration generates a plurality of discreet lengths at which the axial support 16 may be telescoped and locked.

Referring to FIG. 1A, the distal support structure 12 is configured to apply tension to the damaged limb by application of compression force to the top of the foot. The distal support structure 12 is configured as a cuirass that opens and surrounds the lower leg just above the foot. The distal support structure 12 is closeable after surrounding the lower leg and locks in place using apparatus such as, but not limited to, a clamp, clip, buttons, snap, belt and buckle, VELCRO® or other hook and loop fabric fastener, and the like. The distal support structure 12 is cushioned by comprising structures such as, but not limited to, padding, foam, gel or fluid-filled pillows, air or liquid inflatable donut, or the like. The distal support structure 12 applies compression force to the top of the foot, thus generating a traction force on the leg. The distal support structure 12 evenly distributes the applied traction force for maximum comfort and minimum trauma to the foot. The distal support structure 12 is affixed to the lower or distal end of the axial support 16 so that it does not distort or undergo torsion and remains in a plane generally perpendicular to the axis of the axial support 16.

Referring to FIG. 1A, the proximal support structure 14 is configured to be closeable after surrounding the leg and locks in place using apparatus such as, but not limited to, a clamp, clip, buttons, snap, belt and buckle, VELCRO® or other hook and loop fabric fastener, and the like. The proximal support structure 14 generates compression force toward the body and, in concert with the distal support structure 12, generates traction on the leg. The proximal support structure is configured so as not to undergo torsion or distortion out of its primary plane, which is generally orthogonal to the axis of the axial support 12.

Referring to FIG. 1A, the axial support 16 is fabricated preferably from Radiolucent materials so that X-rays or fluoroscopic images may be taken of the limb without undue obscuration of the image by radiopaque denseness of the material. The axial support 16 and all other components of the traction splint 10 are preferably fabricated from materials that are non-magnetic and thus do not generate image distortion, heat, or motive force while being imaged by magnetic resonance imaging (MRI). Preferred materials for fabrication of the axial support and structural members of the proximal support structure 14 and distal support structure 12 include, but are not limited to, carbon fiber, fiber composites, polyurethane, polyethylene, polyvinyl chloride, polypropylene, fiberglass, polycarbonate, polyimide, glass-filled polymers, and the like. The wall thickness shall be thin enough that radiodensity is minimized and radiograph clarity is maximized. The axial support 16 and other structural members of the traction splint 10 shall comprise sufficient integrity to generate and maintain between 1 and 100 pounds of traction force on the limb, preferably between 5 and 50 pounds of traction force, and most preferably between 7 and 30 pounds of force, without failure or distortion.

Referring to FIG. 1A, the traction force generating mechanism 20 is capable of extending the length of the axial support 16 or moving the proximal support 14 or the distal support 12 relative to the axial support in a controlled manner. Backlash and recoil preferably do not occur. A lever to provide mechanical advantage to make the application of force easy for the caregiver is comprised by the traction force generating mechanism 20. The traction force generating mechanism 20 comprises apparatus such as, but not limited to, a jack-screw, a cam, an adjustable or unadjustable spring, an adjustable or unadjustable magnetic attractor, a pneumatic or hydraulic cylinder, a pneumatic bellows, and the like. In one embodiment, the traction force generating mechanism 20 comprises a coarse adjustment and a fine adjustment. The coarse adjustment may be accomplished by apparatus such as telescoping bars with pins and holes, a cam, a gear, or other device known to persons skilled in the art of applying force. A fine adjustment is accomplished using gears with finer tooth spacing or other devices with mechanical advantage whose control surfaces move considerably further than the structural elements that exert the traction force. Once the traction force has been applied, it is maintained by the traction force generating mechanism 20 until the caregiver releases the force. A lock or other device is preferably comprised by the traction force generating mechanism 20 to ensure that the traction force is maintained until relief is desired.

Referring to FIG. 1A, the traction force measuring mechanism 22 is a device such as, but not limited to, a force gauge, a strain gauge, a pressure gauge, an optical interferometer, or the like. The traction force measuring mechanism 22 comprises a display such as, but not limited to, a digital readout, a CRT, a flat panel display, an LCD, optical indicator such as a series of LEDs, and the like. The traction force measuring mechanism 22 optionally comprises an audio output device. The audio output device or the visual display are configured to notify the operator of the traction force being generated as well as other system parameters such as battery power, system status, and the like. Any visual displays are preferably configured to be read in low-light environments and when conditions are inclement such as in the rain, snow, etc.

Figure 1B:
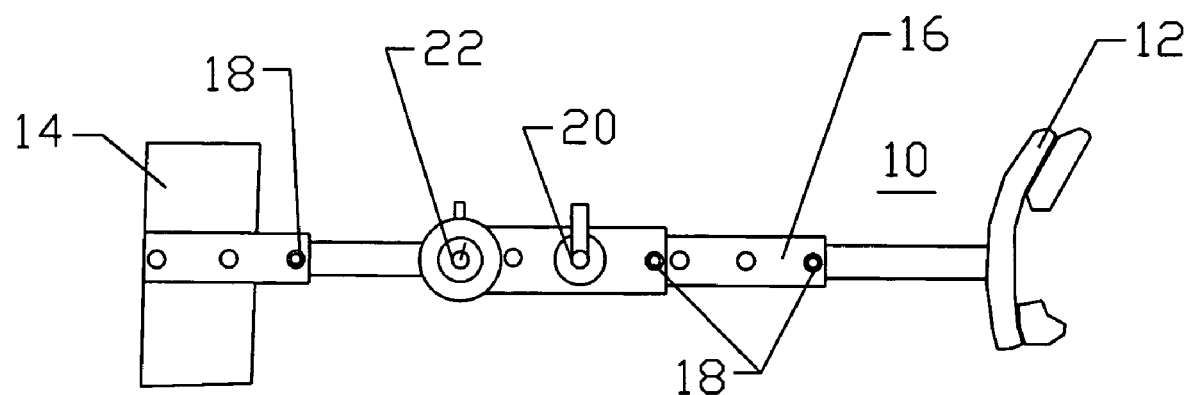
FIG. 1B illustrates a side view of a leg traction splint in its expanded or deployed configuration, according to an embodiment of the invention.

FIG. 1B illustrates a traction splint 10 of the present invention in its fully expanded configuration. The traction splint 10 further comprises a distal support member 12, a proximal support member 14, an axial support 16, one or more axial support locks 18, a traction force generating mechanism 20 and a traction force measuring mechanism 22.

Referring to FIG. 1B, the axial support 16 further comprises telescoping members that slide axially with respect to each other without becoming misaligned. The axial support 16 locks at discreet locations using the plurality of axial support locks 18. A set-screw arrangement, in another embodiment, permits continuously variable axial support 16 extension with locking capability.

Figure 1C:
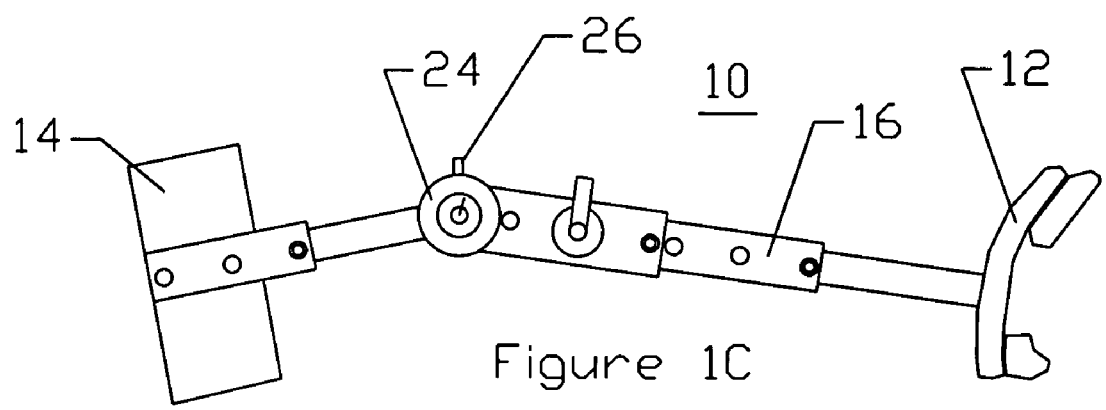
FIG. 1C illustrates a side view of a leg traction splint in its expanded configuration and with its central section articulated at a small angle, according to an embodiment of the invention.

FIG. 1C illustrates a traction splint 10 of the present invention in its fully expanded configuration but articulated at a point along the axial support 16. The traction splint 10 further comprises a distal support member 12, a proximal support member 14, an axial support 16, an articulation joint 24 and an articulation lock 26.

Referring to FIG. 1C, the articulation joint 24 is affixed to the axial support 16 at a point intermediate to its proximal and distal end. The articulation joint 24 provides a pivot point to rotate, bend, or articulate the axial support 16 to provide maximum support benefit to the limb. The articulation joint 24 further comprises an articulation lock 26 that may be selectively and controllably locked and unlocked to maintain the desired amount of articulation or bending.

Figure 2A:
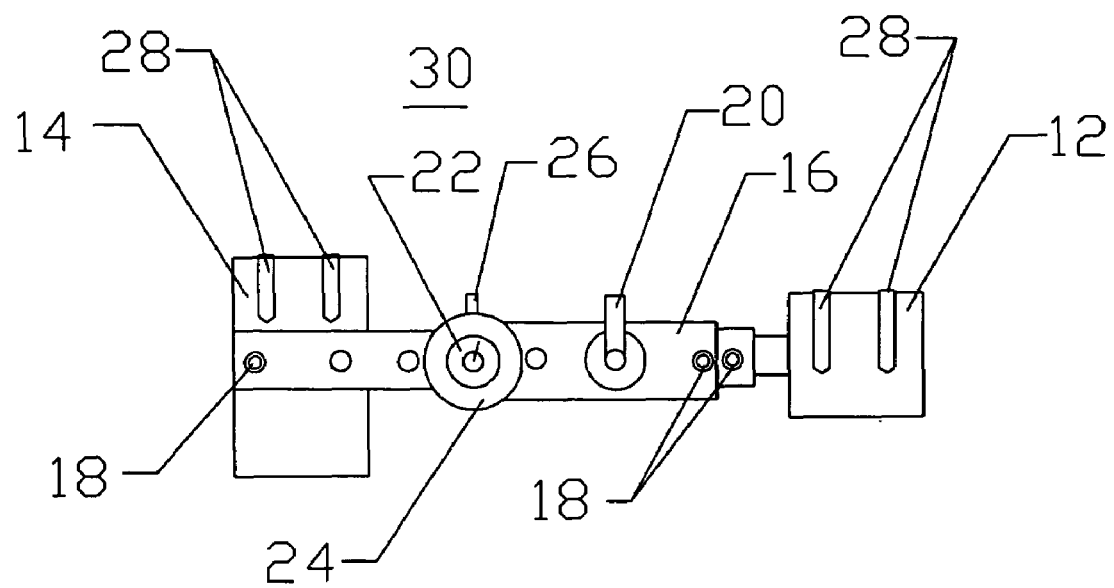
FIG. 2A illustrates a side view of an arm traction splint in its collapsed or storage configuration, according to an embodiment of the invention.

FIG. 2A illustrates a traction splint 30 of the present invention, configured for use on an arm, in its compressed or retracted configuration. The arm traction splint 30 further comprises a distal support member 12, a proximal support member 14, an axial support 16, a plurality of axial support locks 18, a traction generating mechanism 20, a traction measuring mechanism 22, an articulation joint 24 and an articulation lock 26. The proximal support member 14 and the distal support member 12 further comprise a plurality of locking straps 28.

Referring to FIG. 2A, the arm traction splint 30 is configured similarly as for a leg traction splint 10 except that the arm traction splint 30 is shorter overall and the proximal support member 14 and the distal support member 12 are smaller in diameter to accept the arm rather than the leg. The distal support member 12 is configured to surround the patient at or above the wrist to generate the traction force on the arm. The articulating joint 24 is configured to reside at or near the elbow. An intermediate support (not shown) is optionally comprised by the arm traction splint 30 to stabilize the arm in the central region of the arm traction splint 30. The plurality of axial support locks 18 are engaged into locking holes in the axial support 16 to maintain the compressed configuration.

Figure 2B:
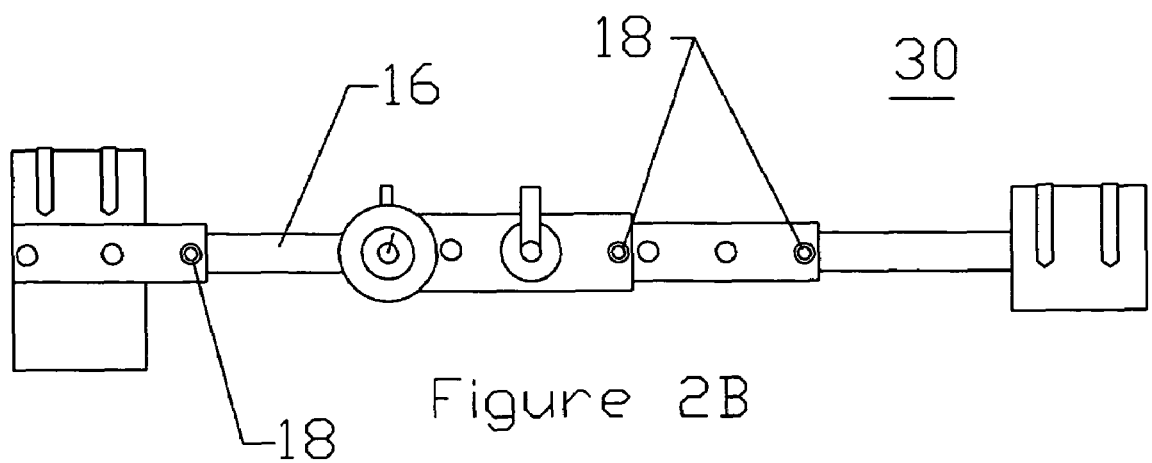
FIG. 2B illustrates a side view of an arm traction splint in its deployed or expanded configuration, according to an embodiment of the invention.

FIG. 2B illustrates the arm traction splint 30 in its fully expanded configuration. Referring to FIGS. 2A and 2B, the plurality of axial support locks 18 are engaged into locking holes in the axial support 16 to maintain the expanded configuration.

Figure 3A:
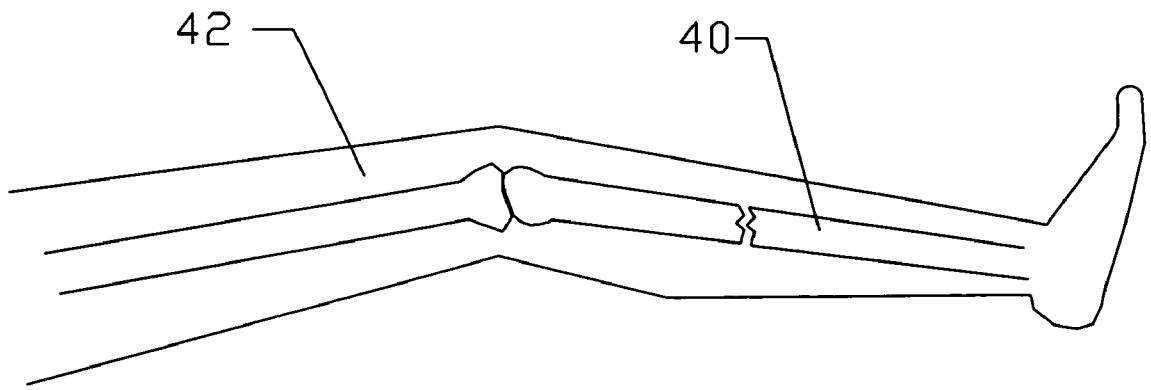
FIG. 3A illustrates a side view of a leg with a fracture to the tibia or bone of the lower leg, according to an embodiment of the invention.

FIG. 3A illustrates a fracture to a tibia 40, a bone in the lower part of a leg 42.

Figure 3B:
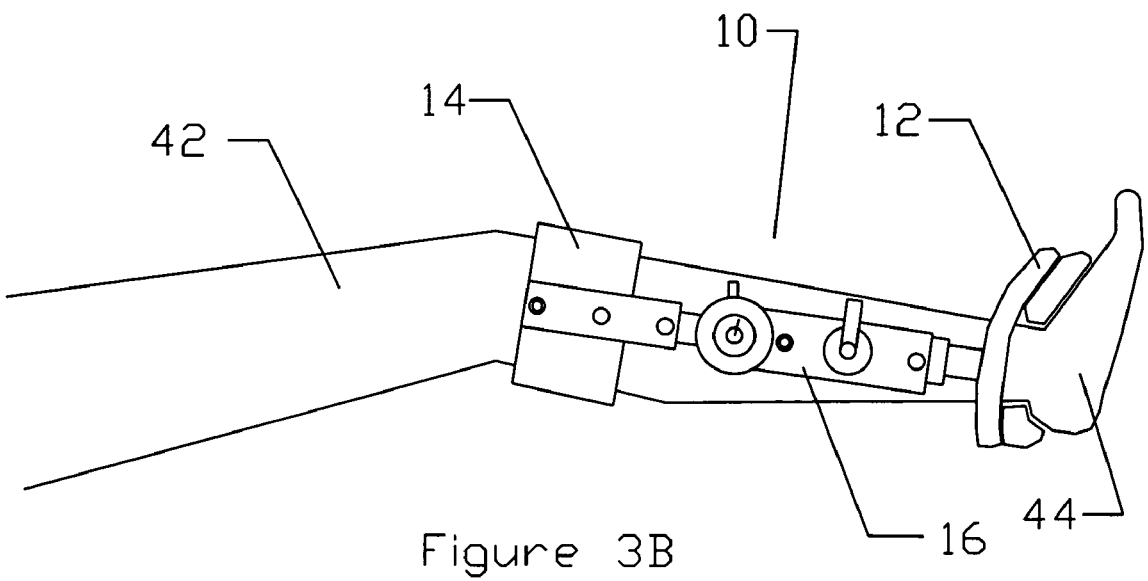
FIG. 3B illustrates a side view of a leg traction splint with traction applied to treat a fracture of the tibia, according to an embodiment of the invention.

FIG. 3B illustrates the fracture to the tibia (not shown) in the lower part of the leg 42 with a leg traction splint 10 applied. Referring to FIGS. 1A, 3A, and 3B, the distal support member 12 engages the top of the foot 44 and generates a caudal or downward force on the foot 44. The proximal support member 14 is engaged with the leg 42 just below the knee, although in another embodiment, it is engaged above the knee. The proximal support member 14 generates cranial or upward force on the leg 42 by friction force, enhanced by compressive force on the leg and the generally outward taper of the leg 42 moving from the foot 44 to the pelvis. The fractured tibia 40 (not shown) is relieved of compressive stresses by the traction splint 10. The axial support 16 is slightly, but not fully, expanded in this configuration.

Figure 4A:
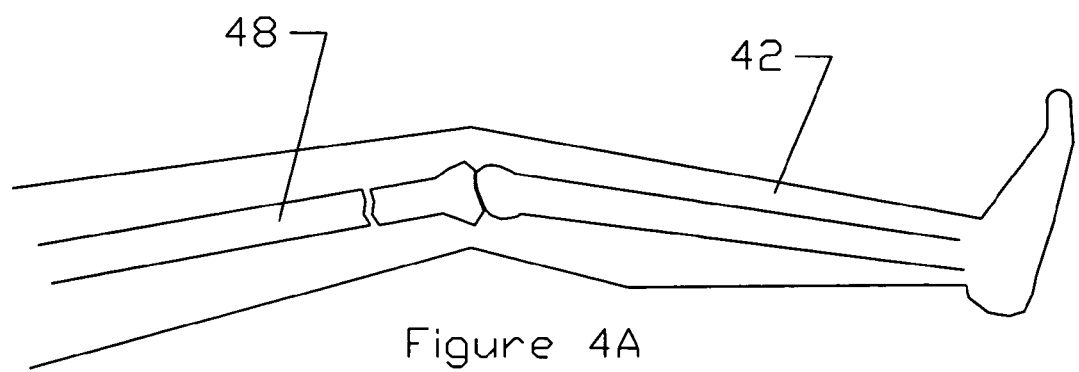
FIG. 4A illustrates a fracture of the lower femur, or bone of the upper leg, according to an embodiment of the invention.

FIG. 4A illustrates a fracture to the lower part of a femur 48, a bone in the upper part of a leg 42.

Figure 4B:
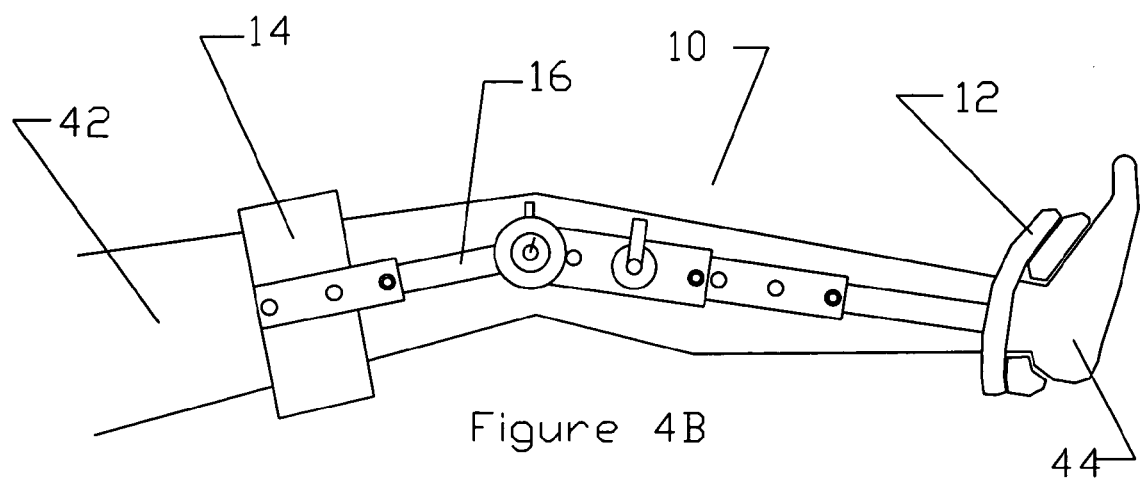
FIG. 4B illustrates a side view of a leg traction splint with its limb contacting regions adjusted to treat a fracture of the lower femur, according to an embodiment of the invention.

FIG. 4B illustrates the fracture to the femur (not shown) in the upper part of the leg 42 with a leg traction splint 10 applied. Referring to FIGS. 1A, 4A, and 4B, the distal support member 12 engages the top of the foot 44 and generates a caudal or downward force on the foot 44. The proximal support member 14 is engaged with the upper part of the leg 42 in the middle of the thigh, although in another embodiment, it is engaged at the ischium of the pelvis. The proximal support member 14 generates cranial or upward force on the leg 42 by friction force, enhanced by compressive force on the leg and the generally outward taper of the leg 42 moving from the foot 44 to the pelvis. The fractured femur (not shown) is relieved of compressive stresses by the traction splint 10. The axial support 16 is nearly, but not completely, expanded in this configuration.

Figure 5A:
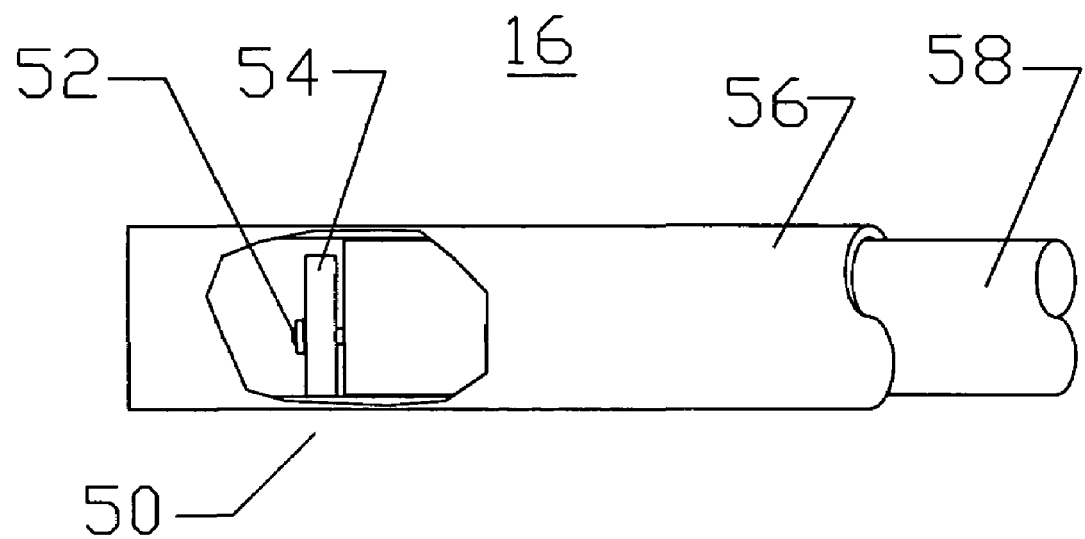
FIG. 5A illustrates a side view of a leg traction splint expansion locking mechanism comprising an offset cam, according to an embodiment of the invention.

FIG. 5A illustrates one embodiment of a locking mechanism 50 for the telescoping axial support 16. The locking mechanism 50 is an offset cam that comprises an axle 52, an offset cam lock 54, an exterior tube 56, and an interior tube 58.

Referring to FIG. 5A, the exterior tube 56 and the interior tube 58 are axially elongate. They are preferably round in cross-section and have an interior and an exterior surface but they may also be slightly elliptical or oval in cross-section. They may even be square or rectangular in cross-section in areas not near the offset cam 50. They slideably move axially relative to each other and also move rotationally relative to each other. The axle 52 is affixed to the end of the interior tube 58. The offset cam lock 54 is a circular, elliptical, or oval component that frictionally engages the interior of the exterior tube 56. The axle 52 projects through a hole in the offset cam lock 54, the hole being located off center of the offset cam lock 54. By manually or remotely telescoping or axially moving the exterior tube relative to the interior tube 58, the desired length is selected. By manually or remotely rotating the interior tube 58 relative to the exterior tube 56, the offset cam lock 54 is compressed against the interior of the exterior tube 56 with increasing force and friction to prevent further axial motion. Counter rotating the two tubes in the other direction will relieve the friction and eliminate the lock between the interior tube 58 and the exterior tube 56.

Figure 5B:
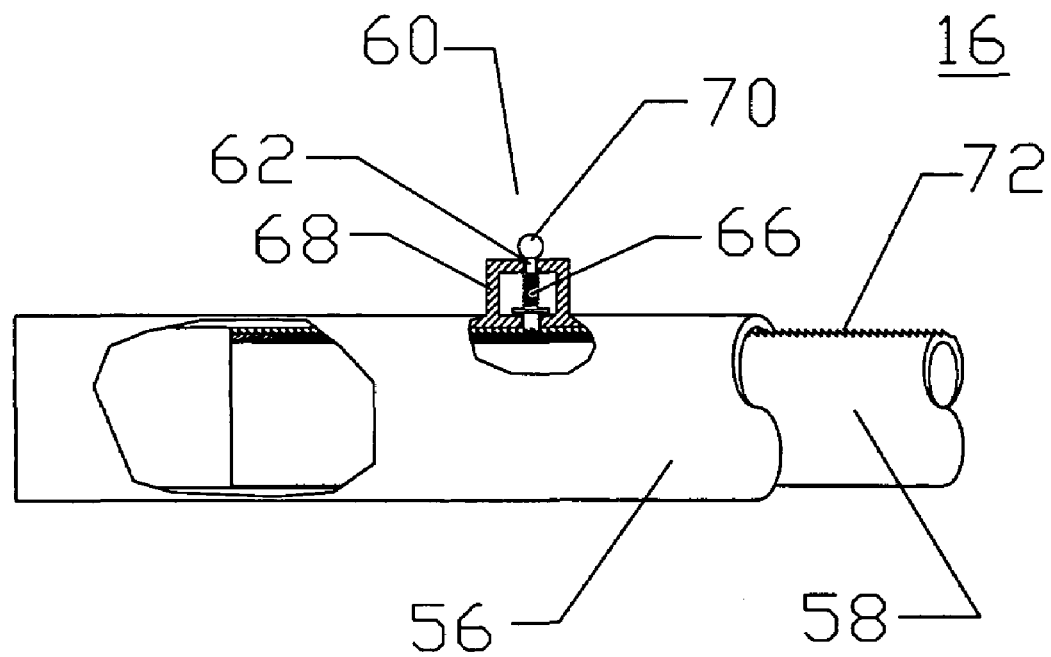
FIG. 5B illustrates a side view of another embodiment of a leg traction splint expansion locking mechanism comprising a spring-loaded pin and engagements, according to an embodiment of the invention.

FIG. 5B illustrates one embodiment of a locking mechanism 60 for the telescoping axial support 16. The locking mechanism 60 is a spring loaded pin lock that comprises a pin 62, a linear line of teeth 72, a spring 66, a lock housing 68, a knob 70, an exterior tube 56, and an interior tube 58.

Referring to FIG. 5B, the interior tube 58 is axially elongate and slides axially with respect to the exterior tube 56, which is also axially elongate. The interior tube 58 and the exterior tube 56 are generally hollow with an interior wall and an exterior wall but they need not be complete tubes, nor need they be round in cross-section. The lock housing 68 is affixed to the exterior tube 56 and supports the pin 62 and the spring 66. The knob 70 is permanently affixed to the outermost part of the pin 62. The spring 66 is trapped by the pin 62 and the lock housing 68 so as to generate an inwardly biased compressive force on the pin 62. The pin 62 engages with teeth 72 on the interior tube 58 to engage the lock. To disengage the lock, the pin 62 is withdrawn manually, by the knob 70, against the spring 66 and away from the teeth 72 on the interior tube 58. The interior tube 58 and the exterior tube 56 are now slidably movable relative to each other and may be relocked at a different location. Preferably the interior tube 58 is not rotationally movable relative to the exterior tube 56. Preferably, the pin 62 has multiple edges on its innermost end to facilitate entry into the teeth 72. In another embodiment, a ratchet mechanism is provided to allow the interior tube 58 to slide in one direction only relative to the exterior tube 56 without withdrawing the pin 62. To move in the other direction, the direction of the compressive force generated by a traction mechanism, the pin 62 must be withdrawn. In yet another embodiment the line of teeth 72 on the interior tube 58 is replaced by a plurality of holes through which the pin 62 selectively projects when aligned with the holes.

Figure 6A:
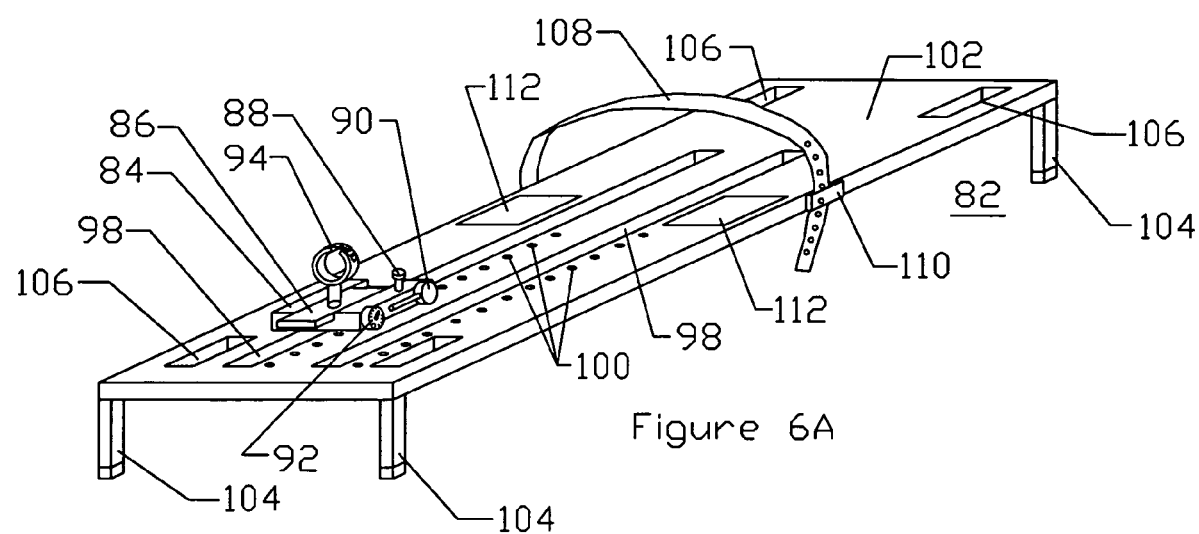
FIG. 6A illustrates an oblique view of a leg traction splint integrated with a backboard, according to an embodiment of the invention.

FIG. 6A illustrates a traction splint 80 integrated with a backboard 82. The traction splint 80 further comprises a lock down plate 84, a traversing stage 86, a lock down pin 88, a traction generating mechanism 90, a traction measuring mechanism 92, and a distal support structure 94. The backboard 82 further comprises one or more longitudinal traction slots 98, a plurality of locking holes or detents 100, a main board 102, a plurality of legs 104, a plurality of carrying handles 106, a chest strap 108, and a chest strap lock 110.

Referring to FIG. 6A, the traction splint 80 is slidably affixed to the main board 102 of the backboard 82 through the longitudinal traction slot 98. A projection, affixed to the bottom of the lock down plate 84 passes through the longitudinal traction slot 98 and is terminated with a "T" or other wide profile to retain the lock down plate 84 in close proximity to the main board 102. The lock down pin 88 serves to hold the position of the lock down plate at a desired location by engaging with the holes or detents 100 in the main board 102. The traversing stage 86 is slidably affixed to the lock down plate 84. The traversing stage 86 is permanently affixed to the distal support structure 94. The traction generating mechanism 90 is affixed to the lock down plate 84 and moves the traversing stage 86. The traction generating mechanism 90 comprises a handle, lever, knob, motor, or other manual or remote adjustment mechanism and further comprises gearing or other mechanical advantage to controllably, forcibly, and easily move the traversing stage 86 relative to the lock down plate 84. In another embodiment, the traction generating mechanism 90 is a spring with permanent or adjustable force, or a magnetic attraction system powered by electromagnets or permanent magnets such as those fabricated from neodymium iron cobalt. The height of the distal support 94 is preferably adjustable and reversibly lockable at a desired distance from the main board 102. The height of the distal support 94 is preferably capable of being adjusted above or below the upper surface of the main board 102. Below the main board 102 height settings require an opening or fenestration in the main board for the foot, leg, and distal support 94 to project therethrough. The traction measuring mechanism 92 is a force or pressure readout similar to that described for the leg traction splint in FIGS. 1A, 1B, and 1C. The distal support structure 94 comprises components that are the same as those described in the distal support structure 12 disclosed in FIGS. 1A, 1B, and 1C.

Referring to FIG. 6A, the plurality of legs 104 on the backboard preferably may be folded up against the main board 102 for space-saving in storage. The plurality of legs 104 are able to folded into their perpendicular positions and locked in place. The plurality of legs 104 further preferably comprise telescoping or folding extensions to permit height adjustment and securing or locking at the desired height. The plurality of carrying handles 106 are preferably slots or cutouts in the main board 102, or they may be straps, handles with standoffs, and the like. The chest strap 108 passes around the chest, preferably under the arms and secures the patient's torso to the backboard main board 102. The chest strap 108 is permanently affixed to one side of the main board 102 and reversibly affixed to the other side of the main board 102 using the chest strap lock 110. The chest strap lock may comprise mechanisms such as, but not limited to, VELCRO® or other hook and loop fabric fastener, fasteners, buttons, snaps, buckles and pins to engage holes in the chest strap 108, and the like. The chest strap 108 is fabricated from materials such as, but not limited to, woven materials, solid materials, nylon, polyester, and the like, all, preferably flexible but inelastic. The chest strap 108 serves the function of the proximal support structure 14 in FIG. 1A. It secures the upper part of the patient from moving caudally, while caudal force is being generated by the distal support structure 12. The chest strap 108 may be replaced by, or augmented by bumps, or projections from the main board 102 that are, preferably padded, and fit under the arms of the patient in the region of the armpit. Such projections or bumps also serve to keep the patient from moving caudally under caudal force. The projections or bumps are long enough to firmly engage the patient's underarms and preferably project upward at least half the thickness of the arm and preferably the full thickness of the body at the shoulder.

Referring to FIG. 6A, in another embodiment of the invention, the locking pin 88 has at least one tooth and preferably a plurality of teeth that engage with teeth in the main board. The locking pin 88 may also comprise a cam lock to frictionally engage the main board through a slot rather than holes 100.

Referring to FIG. 6A, the main board 102 and the legs 104 are preferably fabricated from radiotransparent or radiolucent and non-magnetic materials such as, but not limited to, polyurethane, polyethylene, polypropylene, polystyrene, polyvinyl chloride, acrylics, polyimides, carbon composites, cardboard, corrugated cardboard, fiberboard, wood, foamed materials, glass or other material reinforced polymers, and the like.

Referring to FIG. 6A, the main board 102, in another embodiment, further comprises a standoff or rest that is placed under the knee of the patient to raise the leg, support the knee from below, and maintain a prescribed amount of bend in the knee whether the leg is under traction or not. The standoff projects upward from the main board 102 and is adjustable or positionable under one or both legs at various positions. The standoff is further capable of being secured or locked to the main board 102.

Referring to FIG. 6A, in yet another embodiment, the main board 102 further comprises a pad 112 of foam or elastomeric material that is positioned under the hip. The surface of the foam or elastomeric material further comprises ripples, dimples, or other structures that enhance friction with the patient. The weight of the patient causes the pad 112 of foam or elastomeric material to deform and frictionally support the pelvis so that it does not slide or translate relative to the main board 102 when the leg is placed under traction. The foam or elastomeric pad 112 is fabricated from standard low durometer materials such as, but not limited to, C-flex, polyurethane foam, polyvinylchloride foam, and the like. The foam is preferably closed-cell but could be open cell and is further preferably enhanced by a surface coating of mildly adhesive materials to increase the surface friction against the patient. The pad 112 deforms and extrudes between the legs and the contours of the body to assist in generating friction between the patient and the backboard 82.

Referring to FIG. 6A, the backboard 82 may further comprise wheels and a yoke so that one person can attach themselves to the backboard and pull the backboard along on the wheels, preferably with their hands free. The backboard 82 may further comprise skids or runners suitable for use in snow or ice. The backboard 82 may further comprise inflatable compartments or hollow internal structure that provides buoyancy or flotation to the backboard 82 and a person carried thereon. The backboard 82 may be foldable laterally and or longitudinally. The backboard 82 may be collapsible and inflatable using air. The wheels may be spherical and roll in sockets rather than disc-shaped and on axles. The backboard 82 may comprise a covering to secure the patient thereon. The covering may comprise materials such as Kevlar that are resistant to penetration and thus protect the patient from external dangers. The hollow wheels, disc-shaped or spherically shaped, may serve as flotation devices for the backboard 82. In a preferred embodiment, the hollow spherical wheels are constrained within hemispherical wheel wells that allow for multi-axis rotation. The wheels may, otherwise, be affixed to the backboard 82 by axles or axles and pivots. The backboard 82, of this embodiment, is especially well suited to military applications so that a single soldier can remove an injured soldier to safety without the need for additional help in carrying the stretcher. The single soldier can further carry and use a weapon while transporting the injured soldier since the transporting soldier has their hands free during transport. The backboard 82 may further comprise compartments to hold medications and medical instruments such as bandages, sutures, scalpels, syringes, inflatable splints, traction splints, forceps, food, batteries, heat generation sources, and the like.

Figure 6B:
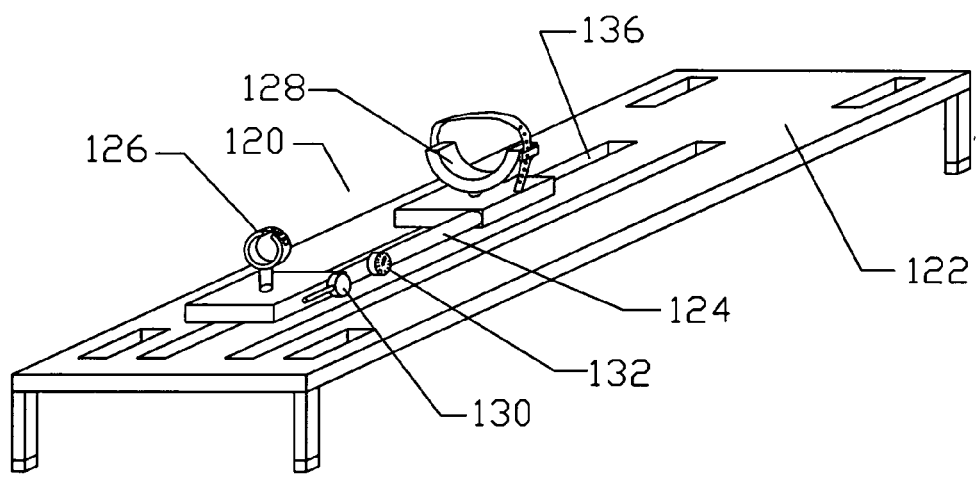
FIG. 6B illustrates an oblique view of a leg traction splint removably integrated with a backboard, according to an embodiment of the invention.

FIG. 6B illustrates a traction splint 120 removably affixed to a compatible backboard or stretcher 122. The traction splint 120 further comprises an axial support 124, a distal support 126, a proximal support 128, a traction generating mechanism 130, a traction measuring mechanism 132, a backboard attachment mechanism 134 (not shown), and an attachment slot 136.

Referring to FIG. 6B, the traction generating mechanism 130 is the same as that described in FIG. 1A or, in another embodiment, the same as that described in FIG. 6A. The distal support 126 is the same as that described for FIG. 1A or 6A. The backboard attachment mechanism 134 is, for example, a spring-loaded T-clamp that is inserted through holes in the proximal support 128 and the distal support 126. The backboard attachment mechanism 134 projects through the attachment slot 136 and is rotated so that a wide flange or "T" structure interferes with the slot and prevents the proximal and distal supports from being withdrawn away from the backboard 122. The backboard attachment mechanism 134 preferably comprises a handle that allows for manipulation of the attachment mechanism 134 to lock and unlock the traction splint 120 from the backboard 122. In other embodiments, the backboard attachment mechanism 134 comprises a VELCRO® or other hook and loop fabric fastener, fastener system, a snap, a buckle, a button, a strap, a magnetic latch, or the like. The proximal support mechanism 128 comprises, in a preferred embodiment, a friction pad affixed to the backboard or stretcher and a strap or other structure that forces or coerces the torso, which further comprises the thorax, abdomen, or pelvis, against the friction pad. The proximal support mechanism 128 of this embodiment gently supports the patient and allows the distal support 126 to provide the desired traction to provide the required stabilization function.

Referring to FIG. 6B, the traction measuring mechanism 132 is optional as is the case on all the traction splints of the present invention. The traction measuring mechanism 132 is preferably optional if the level of traction is pre-set such as with a spring or a pre-calibrated adjustment.

Figure 7A:
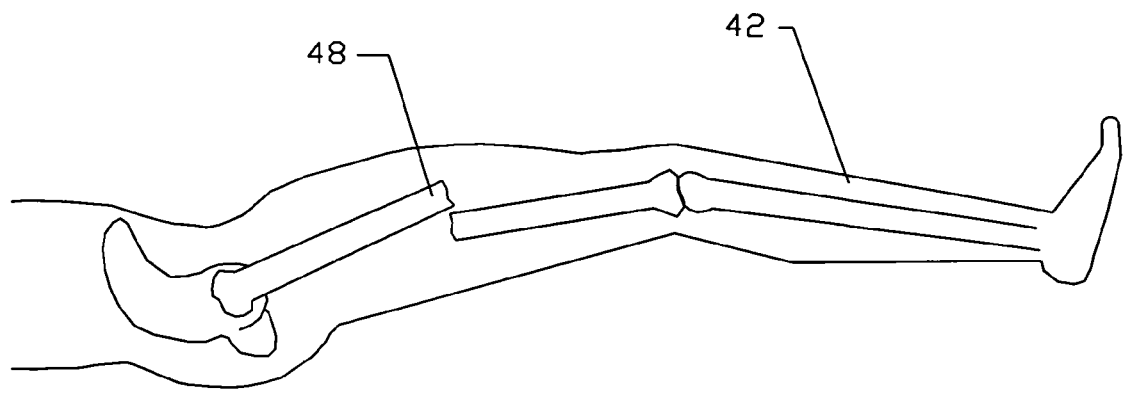
FIG. 7A illustrates a fracture to the upper femur, according to an embodiment of the invention.

FIG. 7A illustrates a fracture to the middle or upper part of a femur 48, a bone in the upper part of a leg 42.

Figure 7B:
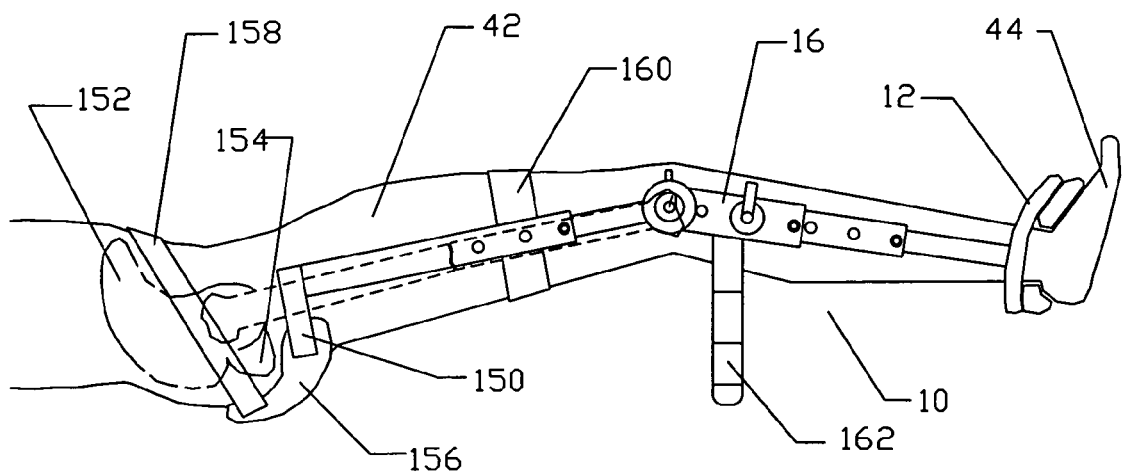
FIG. 7B illustrates a fracture to the upper femur being treated with a leg traction splint comprising an ischial saddle, a foot saddle, and an intermediate support, according to an embodiment of the invention.

FIG. 7B illustrates the fracture to the femur (not shown) in the upper part of the leg 42 with a leg traction splint 10 applied. Referring to FIGS. 1A, 4A, and 4B, the distal support member 12 engages the top of the foot 44 and generates a caudal or downward force on the foot 44. The proximal support member 150, or proximal limb support member, is engaged with the pelvis 152 at the ischium 154. The proximal support member 150 generates cranial or upward force on the leg 42 by direct compression on the ischium 154. The fractured femur 48 (not shown) is relieved of compressive stresses by the traction splint 10. The axial support 16 is completely, expanded in this configuration. The proximal support 150 is engaged with the ischium 154 by a padded bar 156 and a strap 158 to secure the padded bar 156 against the ischium 154. The strap 158 is secured by standard fasteners including those comprising buckles, snaps, buttons, VELCRO® or other hook and loop fabric fastener, and the like. The leg traction splint 10 further comprises a central support 160 and a standoff 162. The central support 160 is a padded or unpadded strap, preferably padded, that stabilizes the leg 42 at the central region of the leg traction splint 10 and maintains close proximity between the leg 42 and the leg traction splint 10. The standoff 162 preferably folds up parallel to the axial support 16 and locks in place when not in use. The standoff 162 is selectively adjustable and foldable to an orientation generally perpendicular or at an angle to the axial support 16 and locks in place at the desired orientation. The standoff 162 further preferably comprises telescoping or adjustable height that is lockable at a desired length. The standoff 162 comprises feet or non-damaging end so as not to rip or damage the surface upon which it rests.

Figure 8A:
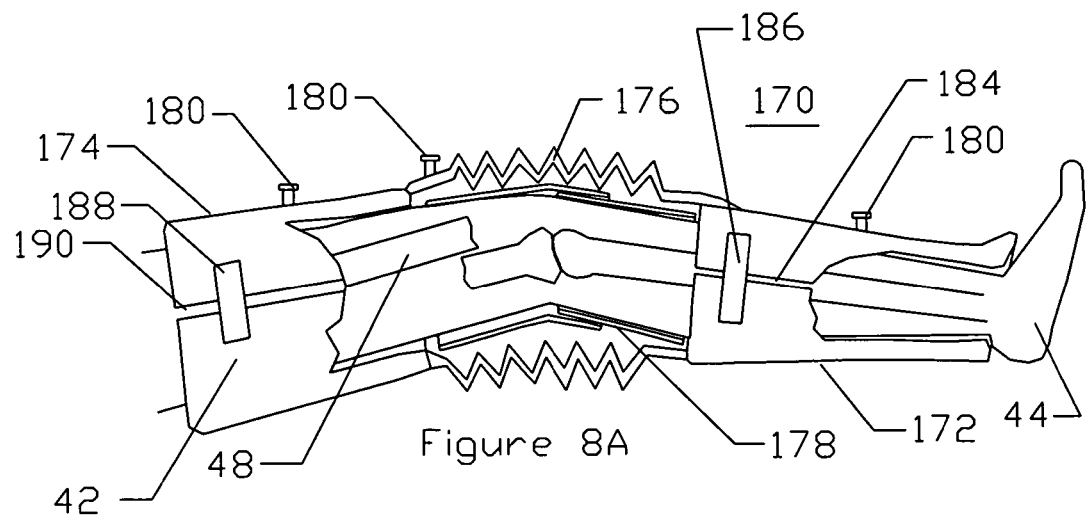
FIG. 8A illustrates a deflated traction splint comprising an inflatable structure applied to a leg, according to an embodiment of the invention.

FIG. 8A illustrates another embodiment of the leg traction splint 170 utilizing inflatable components. The leg traction splint 170 comprises a distal support 172, a proximal support 174, a traction bellows 176, and a protective sleeve 178. The distal support 172 further comprises a distal support opening 184 and a closure device 186. The proximal support 174 further comprises a proximal support opening 190 and a proximal closure device 188. The distal support 172, the proximal support 174, and the traction bellows 176 all further comprise inflation ports and valves 180. FIG. 8A further depicts the traction splint 170 being applied to treat a leg 42, with a foot 44, comprising a fracture to the lower part of the femur 48. The traction splint 170 has been applied to the leg 42 but not inflated in FIG. 8A.

Referring to FIG. 8A, the distal support 172, or distal limb support member, surrounds the leg 42 just above the foot 44. The proximal support 174, or proximal limb support member, surrounds the upper leg and is preferably engaged against the pelvic region at its proximal-most end. In the case of a hip fracture, the proximal support 174 is engaged with the torso of the patient, or an area proximate the arms, above the region of the hip. Both the distal support 172 and the proximal support 174 are preferably C-Shaped, or flat, flexible, wrappable, inflatable structures, with openings 184 and 190, respectively, that are oriented, or aligned, along the axis of the limb. The distal support 172 and the proximal support 174 are wrapped around the limb or leg 42 and secured in place with closure devices 186 and 188, respectively, such as, but not limited to, straps, belts, snaps, buttons, fasteners, VELCRO® or other hook and loop fabric fastener, or the like. The closure devices 186 and 188 are used to secure the opening or openings so as to enclose the limb within the central lumen of the distal support 172 or proximal support 174. In the embodiment where belts are used, the belts can be tightened and fastened to permit adjustment of the distal support 172 and the proximal support 174 to varying limb and body sizes. The C-shaped inflatable structures generally comprise an outer wall and an inner wall, sealed together or integral to each other and an inflatable chamber or space therebetween. An inflation port and valve 180 allows for pressurized gas or liquid to be inserted or injected into the chamber or space. Once the fluid (gas or liquid) has been injected into the chamber or space, the valve prevents escape. The valve 180 is an openable valve such as a stopcock or it preferably is a one-way valve that permits inflation with automatic prevention of fluid escape. A manual override to deflate the chamber is preferred.

Figure 8B:
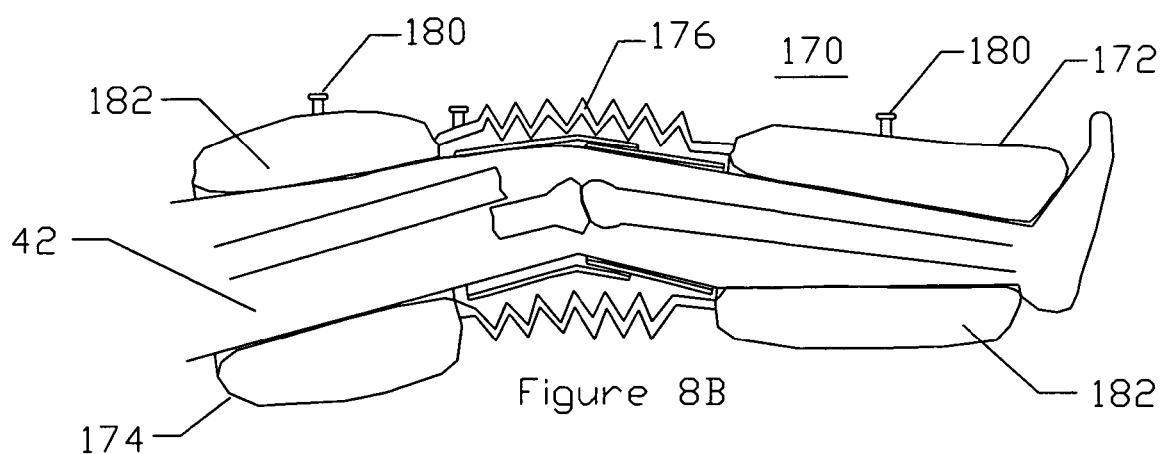
FIG. 8B illustrates a traction splint comprising an inflatable structure applied to the leg and inflated at the ends for stabilization, according to an embodiment of the invention.

FIG. 8B illustrates the leg traction splint 170 with the proximal support 174 and the distal support 172 inflated and the plurality of chambers 182 are also shown. By optionally inflating the chamber 182 the inner wall is forced against the leg 42, which causes that section of the leg 42 to be stabilized and secured. The inner wall further causes frictional forces to exist that prevent relative motion of the proximal support 174 and distal support 172 relative to the leg 42 once traction force has been generated. The leg traction splint 170 preferably also comprises a standoff (not shown), inflatable or non-inflatable, to position the leg 42 relative to a gurney, backboard, bed or stretcher. The traction bellows 176 has not yet been inflated and traction has not yet been applied to the leg 42. The proximal support 174, the distal support 172, and the traction bellows 176 can be fabricated from materials such as, but not limited to, polyvinyl chloride, polyethylene, polypropylene, polyurethane, polyester, polyimide, and the like. The proximal support 174 and the distal support 172 can range in axial length from 1 inch to 20 inches and preferably between 2 inches and 10 inches. The inside diameters of the proximal support 174 and the distal support 172, when fastened into a collar or cylinder, can range between 1 inch and 30 inches, depending on the limb or body part being encompassed by the support 174 and 172. In a preferred embodiment, the proximal support 174 and the distal support 172 have adjustable diameters, which can be changed by tightening or cinching belts that close the openings 190 and 184, respectively.

The wall thickness of the proximal support 174, the distal support 172, and the traction bellows 176 can range from 0.001 inches to 0.01 inches. The wall thickness and material selection for each of the regions, the proximal support 174, the distal support 172, and the traction bellows 176 can be different or vary. For example, the traction bellows 176 may require a thicker wall to sustain the pressures necessary to generate traction, than would the wall of the proximal support 174 whose function it is only to grip the patient. The traction bellows 176 can be a simple airbag that expands one or more of its lengths. The traction bellows 176 can be a simple cylinder that is size limited in its lateral dimension but at less than full inflation pressure, can change its axial dimension as a function of inflation pressure and traction applied to a limb. In an embodiment, the traction bellows 176 is a cylindrical bag with a diameter of 2.0 inches and a length of 18 inches. When filled with air at a pressure of 15 pounds per square inch (PSI), the traction bellows 176 can apply approximately 47 pounds of traction force as long as the length between the proximal limb support 174 and the distal limb support 172 permits the cylindrical bag to not fully expand to 18 inches in length. The traction bellows 176 wall thickness and seam strength are chosen so as to be able to resist the 15 PSI pressure, preferably with a safety factor of 1.5 or greater. Any seams or connections, used to fabricate the inflatable traction splint 170, can be created by heat-sealing the flexible, polymeric bag materials or using adhesives such as cyanoacrylate, UV curable polyurethane adhesive, or the like. In another embodiment, the traction bellows 176 comprises two or more cylindrical bags distributed around the limb to provide an even traction without generating any torsion, or bending. For example, two cylindrical bags can be distributed one on the inside of a leg and one on the outside of the leg. A plurality of traction bellows 176, or bags, can be operably connected by a manifold so that they are simultaneously inflated to the same pressure. In another embodiment, the plurality of traction bellows 176 are separately inflated to provide control over bending of the limb in the region of damage.

Figure 8C:
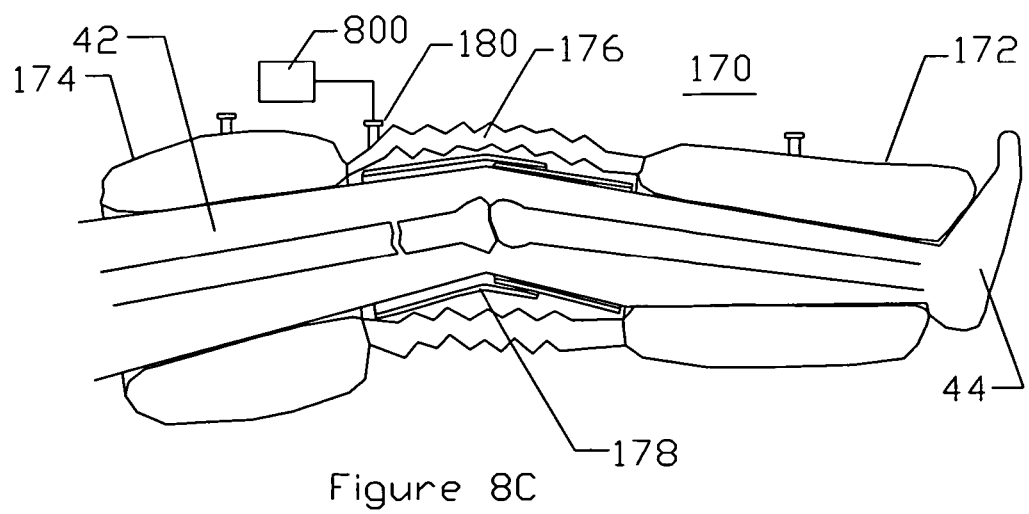
FIG. 8C illustrates a traction splint comprising an inflatable structure applied to the leg and inflated at the ends for stabilization, the central longitudinally expansible region further pressurized to generate traction on the leg, according to an embodiment of the invention.

FIG. 8C illustrates the leg traction splint 170 with the proximal limb support or proximal support 174, the distal limb support or distal support 172, and the traction bellows 176 inflated or pressurized. The inflation ports 180 on the distal support 172 and the proximal support 174 can be separate or they can be operably connected by a manifold (not shown) so that they are inflated at the same time by a single inflation device through a single inflation port or valve (not shown). The optional protective sleeve 178 can surround the leg or arm and resides between the leg 42 and the traction bellows 176. The protective sleeve 178 can provide outwardly directed resistance against any inward forces that might be created by the inflatable traction bellows 176. The protective sleeve 178 in a preferred embodiment comprises two or more segments that telescope against each other to permit longitudinal motion of the leg 42 inside the traction splint 170. The protective sleeve 178 is loosely applied to the leg 42 and does not provide any inward force against the leg 42. The protective sleeve 178 is axially elongate and is preferably open on one side by way of a slit or slot so it can be placed on the leg 42, or it is slid onto the leg 42 over the foot 44 and therefore not need to be slotted axially. The protective sleeve 178 may not be required where the traction splint 170 comprises a cylindrical or other lateral dimension-controlled, or limited, traction bellows 176. The protective sleeve 178 can be fabricated from polymeric, metallic, or ceramic materials such as stainless steel, aluminum, fiberglass, or any of the materials used to fabricate the traction bellows 176.

Referring to FIG. 8C, the traction bellows 176 are disposed between the proximal support 174 and the distal support 172 and exert a separation force on the two supports. The separation or traction force is generated by inflating the traction bellows 176. Inflation of the traction bellows 176 to a specified pressure generates a specific axial force separating the proximal support 174 and the distal support 172. The traction bellows 176 has restricted outward and inward expansion and its primary expansion is in the axial direction only. The restriction on outward and inward expansion of the traction bellows 176 is created by stiffening members and inelastic materials, or by the use of inelastic materials and an expansion limited configuration, such as structures found in angioplasty balloons. Inflation of the traction bellows 176 causes corrugations, undulations, or natural folds in the bellows to straighten out generating a length increase under a force. Inflation is generated through a port and valve 180. Inflation pressure is preferably monitored using a pressure gauge that is integral to or removable from the inflation port 180. The pressure gauge can be calibrated in units of pressure (PSI), force (pounds, Newtons, etc.), or both. The traction generating means, bag, or traction bellows 176 may, in another embodiment, comprise mechanisms such as, but not limited to, hydraulic cylinders, pneumatic cylinders, jack screws, cam levers, and the like. Pneumatic inflation or hydraulic inflation is accomplished using a bulb, foot pump, bicycle pump, syringe, diaphragm pump, or any other type of pump 800. The inflation device 800 suitable for inflating the traction bellows 176, bag, or flexible cavity can be provided separately or can be provided integrally affixed to, and operably connected to, the inlet or inflation port 180 of the traction bellows 176. The inlet or inflation port 180 can be further provided with a one-way valve or it can be provided with a pressure bleed port with a fine adjustment knob to facilitate traction force fine-tuning. The traction bellows 176, or sac, can further comprise stiffeners such as battens, rings, or other means to prevent overexpansion of the traction bellows 176 in a given direction, such as toward the limb.

Application of the radiolucent, collapsible, traction splint system provides improved access to care for patients since said splint is more likely to be carried on an ambulance or helicopter or other emergency vehicle where space is at a premium. The inflatable traction splint can be removably affixed to a backboard using hook and loop fasteners, clips, snaps, caribbeaners, or the like. The application of this traction splint system facilitates analysis of the patient's injuries because the injuries can be diagnosed and analyzed while the traction splint is still attached to the patient and providing the palliative function of removing stress from the injured limb region. This traction splint facilitates damage control procedures because it is more likely to be carried by emergency personnel and is able to continue to function while the patient is being triaged, diagnosed, and treated. Stress removal from the damaged limb is essential to minimize collateral damage to adjacent structures such as blood vessels, nerves, and muscle and the patient is less likely to continue to spiral into shock. Such damage control procedures have been shown to improve patient outcomes and save lives. The inflatable version of the system can be fabricated from inexpensive components, using inexpensive heat seal manufacturing technology, and has the further advantage of folding into an extremely small space such as 2 inch by 4 inches by 4 inches, or smaller, to enhance portability.

The present invention may be embodied in other specific forms without departing from its spirit or essential characteristics. For example, the proximal and distal supports may be cuirass-type devices, pads with straps and belts, or inflatable collars. The traction generating mechanism can be a jack-screw, an inflatable bellows or airbags, electromagnets, permanent magnets, or a pulley system, among other options. The mechanical and pneumatic traction splints may be hybrid and use some of the components of the other type of traction splint. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. An apparatus adapted for generating traction on a limb comprising:
   a proximal limb support member comprising:
      a proximal limb support inflatable structure configured to surround a limb of a patient;
      a proximal inflation port affixed to the proximal limb support inflatable structure for inflating the proximal limb support inflatable structure;
      a proximal limb support opening configured to be disposed along the axis of the limb, said proximal limb support opening configured to allow the limb to be inserted into the proximal limb support;
      a proximal limb support closure device for closing the proximal limb support opening; and
      a proximal inner wall that causes frictional forces to exist that prevent relative motion of the inflated proximal limb support member relative to the limb;
   a distal limb support member, comprising:
      a distal limb support inflatable structure configured to surround the limb of the patient;
      a distal inflation port affixed to the distal limb support inflatable structure for inflating the distal limb support inflatable structure;
      a distal limb support opening configured to be disposed along the axis of the limb, said distal limb support opening configured to allow the limb to be inserted into the distal limb support;
      a distal limb support closure device for closing the distal limb support opening; and
      a distal inner wall that causes frictional forces to exist that prevent relative motion of the distal support member relative to the limb;
   a traction bellows disposed between the proximal limb support member and the distal limb support member, comprising:
      an inflatable, flexible cavity, wherein at least one wall of the inflatable, flexible cavity comprises undulations; and
      a bellows inflation port affixed to the traction bellows for inflating the traction bellows, wherein inflation of the traction bellows causes the undulations in the traction bellows to straighten out generating a length increase of the traction bellows along a longitudinal axis of the limb; and
   an inflation device configured to separately inflate the proximal limb support member, the distal limb support member, and the traction bellows;
   wherein the proximal limb support member is affixed to a first side of the traction bellows and the distal limb support member is affixed to a second side of the traction bellows; and
   wherein the proximal inflatable structure, the distal inflatable structure, and the traction bellows are not operably connected with regard to inflation.

2. The apparatus of claim 1 wherein a protective sleeve surrounds the limb and separates the limb from the traction bellows.

3. The apparatus of claim 2 wherein said protective sleeve comprises telescoping members.

4. The apparatus of claim 1 wherein said traction bellows comprises folds running generally perpendicular to the axis of the limb.

5. The apparatus of claim 1 wherein said distal limb support closure device comprises a strap with a hook and loop fastener.

6. The apparatus of claim 1 wherein said proximal limb support closure device comprises a strap and a hook and loop fastener.

7. The apparatus of claim 1 wherein the inflation device uses air for inflation.

8. An apparatus adapted for generating traction on a limb comprising:
   a proximal limb support member, the proximal limb support member comprising:
      a proximal inflatable structure, wherein at least a portion of the proximal inflatable structure is expandable from a first deflated state to a second inflated state, the proximal inflatable structure in the first deflated state configured to surround a limb of a patient along the axis of the limb;
      a proximal inflation port affixed to the proximal inflatable structure, wherein the proximal inflatable structure is inflated from the first deflated state to the second inflated state through the proximal inflation port;
      a proximal closure device for closing the proximal inflatable structure in the first deflated state around the limb; and
      the proximal inflatable structure further comprising a proximal inner wall configured adjacent to the limb, wherein the proximal inner wall causes frictional forces to exist that prevent motion of the proximal limb support member relative to the limb when the proximal inflatable structure is in the second inflated state;
   a distal limb support member, the distal limb support structure comprising:
      a distal inflatable structure, wherein at least a portion of the distal inflatable structure is expandable from a first deflated state to a second inflated state, the distal inflatable structure in the first deflated state configured to surround the limb of the patient along the axis of the limb;

a distal inflation port affixed to the distal inflatable structure, wherein the distal inflatable structure is inflated from the first deflated state to the second inflated state through the distal inflation port;

a distal closure device for closing the distal inflatable structure in the first deflated state around the limb; and the distal inflatable structure further comprising a distal inner wall configured adjacent to the limb, wherein the distal inner wall causes frictional forces to exist that prevent motion of the distal limb support member relative to the limb when the distal inflatable structure is in the second inflated state;

a bellows member disposed between the proximal limb support member and the distal limb support member, the bellows member comprising:

a bellows inflatable structure, wherein at least a portion of the bellows inflatable structure is expandable from a first deflated state to a second inflated state, the bellows inflatable structure comprising at least one surface having undulations;

a bellows inflation port affixed to the bellows inflatable structure, wherein the bellows inflatable structure is inflated from the first deflated state to the second inflated state through the bellows inflation port;

wherein the undulations straighten out generating a length increase of the bellows member along a longitudinal axis of the limb when the bellows inflatable structure is in the second inflated state; and an inflation device configured to separately inflate the proximal inflatable structure, the distal limb inflatable structure, and the bellows inflatable structure;

wherein the proximal inflatable structure, the distal inflatable structure, and the bellows inflatable structure are not operably connected with regard to inflation.

9. The apparatus of claim 8 wherein a protective sleeve surrounds the limb and separates the limb from the bellows member.

10. The apparatus of claim 9 wherein said protective sleeve comprises telescoping members.

11. The apparatus of claim 8 wherein said bellows member comprises folds configured generally perpendicular to the axis of the limb.

12. The apparatus of claim 8 wherein said distal limb support closure device comprises a strap with a hook and loop fastener.

13. The apparatus of claim 8 wherein said proximal limb support closure device comprises a strap and a hook and loop fastener.

14. The apparatus of claim 8 wherein the inflation device uses air for inflation.

15. A method for generating traction on a limb comprising the steps of:

providing a traction generating apparatus comprising a proximal limb support member, a traction generating member, and a distal limb support member in a first, uninflated configuration where the proximal limb support member, the traction generating member, and the distal limb support member are uninflated;

wrapping the proximal limb support member and the distal limb support member around limb sections on opposite sides of a fracture when the members are in their first, uninflated configuration;

inflating the proximal limb support member to provide friction between the proximal limb support member and the limb, while the traction generating member remains uninflated and no traction is being generated on the limb;

inflating the distal limb support member is to provide friction between the distal limb support member and the limb, while the traction generating member remains uninflated and no traction is being generated on the limb; and inflating the traction generating member, causing a separation force to be imposed on the proximal and distal limb support members;

wherein the separation force is generated by straightening undulations in the traction generating member causing a length increase along a longitudinal axis of the limb.

16. The method of claim 15, further comprising a step of providing a distal inner wall and a proximal inner wall, adjacent to the limb, wherein the distal inner wall and the proximal inner wall exert frictional forces that prevent motion of the distal limb support member and the proximal limb support member relative to the limb when the distal inflatable structure and the proximal inflatable structure are inflated.

17. The method of claim 15 further comprising the step of at least partially surrounding the limb with a protective sleeve which separates the limb from the traction generating member.

18. The method of claim 15 wherein the step of inflating the traction generating member further comprises use of an inflation device.

19. The method of claim 15 further comprising the step of closing openings in the distal limb support member and the proximal limb support member with a closure device.

20. The method of claim 15 wherein the uninflated proximal limb support member, traction generating member, and distal limb support member are provided in a flat, flexible configuration that folds into a small space.

* * * * *